United States Patent [19]

Ertle et al.

[11] Patent Number: 5,160,660
[45] Date of Patent: Nov. 3, 1992

[54] DIHALOHYDANTOIN BLEACH

[75] Inventors: Raymond T. Ertle, Pompton Plains; Robert P. Arbaugh, Westampton, both of N.J.

[73] Assignee: Cap City Products Co. Inc., Kearny, N.J.

[21] Appl. No.: 573,547

[22] Filed: Aug. 27, 1990

Related U.S. Application Data

[63] Continuation-in-part of Ser. No. 776,637, Sep. 16, 1985, Pat. No. 4,973,424.

[51] Int. Cl.$^5$ .......................... C01B 21/083
[52] U.S. Cl. .................. 252/186.34; 252/187.33
[58] Field of Search .......... 252/186.34, 186.36, 252/187.33

[56] References Cited

U.S. PATENT DOCUMENTS

| | | | |
|---|---|---|---|
| 2,795,556 | 6/1957 | Quinn | 252/187 |
| 2,863,800 | 12/1958 | Gottfried | 167/33 |
| 2,938,764 | 5/1960 | Blomfield | 8/108 |
| 3,257,324 | 6/1966 | Wearn et al. | 252/99 |
| 4,058,618 | 11/1977 | Ovchinnikov et al. | 424/273 R |
| 4,167,832 | 9/1979 | Zetterquist et al. | 47/1 R |
| 4,235,599 | 11/1980 | Davis et al. | 252/95 |
| 4,284,524 | 8/1981 | Gilbert | 252/99 |
| 4,382,799 | 5/1983 | Davis et al. | 8/107 |
| 4,534,697 | 8/1985 | Girard | 252/90 |
| 4,713,079 | 12/1987 | Chun et al. | 8/101 |
| 4,867,895 | 9/1989 | Choy | 252/91 |
| 4,973,424 | 11/1990 | Ertle et al. | 252/186.35 |

Primary Examiner—Richard D. Lovering
Assistant Examiner—Joseph D. Anthony
Attorney, Agent, or Firm—Klauber & Jackson

[57] ABSTRACT

An improved dry powder composition for use in aqueous solution in the bleaching and sanitizing of fabrics, which will cause minimal fabric or fabric dye damage upon direct contact of the concentrated composition with damp or wet fabric. The composition includes a first component comprising a dry dihalohydantoin, which in aqueous solution provides a source of available bleaching and sanitizing chlorine; and a second component comprising an inhibiting system in an effective amount to inhibit the activity of available chlorine from the first component such that fabric or fabric dye degradation is beneath a predetermined level when the concentration of the first component of the composition is above saturation with respect to the aqueous solvent. The inhibiting system comprises 5,5-dimethylhydantoin, and one or more dry acidifying agents which function to buffer a 50% aqueous solution/suspension of said composition to a pH of 5.0 or below. The powder composition can be readily formed into highly handleable pellets or granules.

13 Claims, No Drawings

DIHALOHYDANTOIN BLEACH

RELATED APPLICATION

This application is a continuation-in-part of copending application Ser. No. 776,637, filed Sept. 16, 1985 now U.S. Pat. No. 4,973,424.

BACKGROUND OF THE INVENTION

This invention relates generally to the bleaching and sanitizing of fabrics and, more specifically, relates to compositions and methods for effecting such operations with reduced degradation to the fabric and/or dyes contained in the fabrics.

It has long been known in the prior art to bleach and/or sanitize fabrics with various chemical compounds which, in aqueous solution, provide a source of available chlorine. The said available chlorine is normally present in solution as hypochlorous acid or hypochlorite ion, depending upon the pH of the solution.

Among the compounds useful for such purposes are the dihalohydantions. Typical dihalohydantoins include 1,3-dichloro- 5,5-dimethylhydantoin and 1-bromo-3-chloro-5, 5-dimethylhydantoin.

In practical use, however, these compounds have the potential to cause extensive damage to the substrates which are being bleached or sanitized, unless they are used according to a prescribed method. This prescribed method of use normally dictates a set of use conditions which eliminate the possibility of the compounds coming in contact with the substrate while in the concentrated form. For example, in the bleaching or sanitization of laundry, normally performed in a washing machine, according to the usually prescribed method of use, the compounds must be dissolved in the wash water prior to the addition of fabrics to guard against the contact of undissolved or partially dissolved particles of the bleaching compound with the fabric being laundered. This is a marked inconvenience, and requires the constant supervision of the operator to insure that no fabric damage occurs. Should the dihalohydantoins, or formulations containing them, be poured directly onto wet fabrics in the machine under conditions of misuse, extensive damage will occur—in the form of severe dye destruction and/or fabric pinholeing.

In an effort to overcome the damage which thus occurs through the normally expected "misuse" of this type of product, formulators have gone to great lengths to encapsulate the dihalohydantoins, through the use of water soluble coatings, or agglomeration techniques, in an effort to prevent the direct contact of these compounds with the fabric. These methods are expensive, and, at best, only partially prevent the damage which invariably occurs with misuse. The problem of formulating a dry chlorine bleach practical for home use has been the subject of considerable research and has been a long-standing problem in the industry. Although many attempts at commercialization have been made, no successful widely marketed product bearing the necessary attributes currently exists.

The use of the aforementioned dihalohydantoins (DHH) as bleaching agents is disclosed, inter alia, in U.S. Pat. No. 4,713,079 to Chun et al which thus describes the use of these compounds in bleaching particles containing, along with the DHH, a buffering salt and an organic binder. Although these formulations offer a lower damage potential than DHH alone, the compositions taught have the potential to cause significant fabric and dye damage when used, as might be expected, in conjunction with a normally alkaline laundry detergent product, since the combination of the materials under misuse conditions can result in a local pH which is high enough to allow the DHH to cause fabric and dye damage. Additionally, the necessity of adding an organic binder to the compositions complicates the manufacturing process and serves, at an additional expense, only a mechanical function.

Ouinn, U.S. Pat. No. 2,795,556 teaches the production of bleaching compounds based upon dichlorodimethyl hydantoin, through spray drying processes, which are buffered to a pH range of 6-10. This pH range is high enough to cause significant fabric and dye damage under conditions of misuse.

Wearn et al, U.S. Pat. No. 3,257,324 describes a dichloro-dimethylhydantoin bleach which has an aqueous pH of at least 7.5. Misuse damage potential is not addressed, and would most certainly occur.

Zetterouist et al, U.S. Pat. No. 4,167,832 teaches the use of dichloro-dimethylhydantoin in an application for preserving flowers, whereby it is used as a source of chlorine to prevent bacteria formation in the vase water. It is disclosed that the dichloro-dimethylhydantoin splits off chlorine at an increasing rate as the pH of the water falls from a value of 6.8. This is contrary to the findings of the present invention.

In accordance with the foregoing, it may be regarded as an object of the present invention, to provide a composition for use in aqueous solution in the bleaching and sanitizing of fabrics, which, under conditions of misuse, will cause little or no damage to the fabric being treated.

It is a further object of the invention, to provide a method for manufacture of compositions of the foregoing character, which readily produces such compositions in a highly utilitarian pelletized or granulated form; and which can effect such result without the use of organic binders.

SUMMARY OF THE INVENTION

Now, in accordance with the present invention, bleaching and/or sanitizing compositions have been discovered which have the unexpected property of inhibited chlorine activity at high concentrations. Using this discovery, it is, therefore, possible to formulate bleaching and sanitizing compositions which do not require special dose packaging or encapsulating techniques, and which have an extremely low potential for damaging the substrate being sanitized or bleached under conditions of misuse. Normally, the formulations of the invention only exhibit significant inhibition of the activity of the bleaching components at high concentrations, i.e., under misuse conditions, and yet allow the desirable formation of hypochlorous acid and/or hychlorite ion at normal use dilutions. The formulations of the invention also prevent misuse damage when used in conjunction with a normally alkaline laundry detergent and do not require the use of an organic binding agent to produce discrete, easily handleable particles, granules, or pellets.

Pursuant to the invention, an improved composition for use in aqueous solution in the bleaching and sanitizing of fabrics is provided, which comprises a first component comprising a dry dihalohydantoin, which in aqueous solution provides a source of available bleaching and sanitizing chlorine; and a second component comprising an inhibiting system in an effective amount to inhibit the activity of available chlorine from the first component such that fabric or fabric dye degradation is beneath a predetermined level when the concentration of the first component of the composition is above saturation with respect to the aqueous solvent. The inhibiting system comprises 5,5 dimethylhydantoin, and one or more dry acidifying agents which function to buffer a 50% aqueous solution/suspension of the composition to a pH of 5.0 or below. Thus, even under the striking misuse conditions wherein the powder composition, along with a normally alkaline detergent, is in direct contact with a wet fabric, relatively little or no perceptible damage to the fabric, or dye destruction, occurs.

The said first component, which serves as the source of available chlorine, comprises a dihalogenated hydantoin, such as 1,3-dichloro-5,5-dimethylhydantoin; 1,3-dibromo-5,5-dimethylhydantoin, or 1-bromo-3-chloro-5,5-dimethylhydantoin. The second component, i.e. the inhibiting system, comprises a chlorine sink, such as 5,5-dimethylhydantoin, and as the acidifying agent can include a dry weak organic or inorganic acid such as boric acid, which serves to buffer the 50% solution/suspension pH to a value below 5 and to maintain this level of acidity. Other such acids can be used such as citric or oxalic acid. Similarly dry acid buffering salts such as sodium or potassium phosphate, monobasic can be used. Quite surprisingly, the three dry components, when mixed with sufficient water for preparation, form a paste which quickly sets up or hardens, allowing the formation of homogeneous discrete particles by a simple process such as extrusion, without the need for an organic binder. Alternatively a somewhat less viscous mixture with water can be agitated to readily form discrete granules.

Pursuant to the invention, it has unexpectedly been found that minimizing damage to the fabric and dye is strikingly dependent upon providing both the chlorine sink and the buffering effect of the inorganic acid(s) and/or buffering salt(s) in the composition, under the aforementioned "misuse" conditions of saturation.

The composition of the invention can also contain additional inorganic fillers and builders, provided that these ingredients do not cause the pH of the finished formulation to rise above the desired pH.

The aforementioned first component which serves as the source of available chlorine in the composition, will normally be present in sufficient concentration to provide between 0.1 and 1000 ppm available chlorine in the total wash liquor. The weight ratio between the first component, i.e. the dihalogenated hydantoin, and the 5,5-dimethylhydantoin, is generally in the range of from 1:10 to 10:1, and preferably is in the range of 1:2 to 2:1. The dry acidifying agents are employed at a level of 0.5 to 10 parts, and preferably at a level of 1 to 5 parts per 10 parts of total combined dihalohydantoin and dimethylhydantoin.

DESCRIPTION OF PREFERRED EMBODIMENT

Prior art bleaching and sanitizing compositions in the field to which this invention pertains have commonly been used by the consumer by depositing quantities of same in a load of laundry or other fabrics, usually in a household washing machine. Unless the procedures for use recommended by the manufacturer of these compositions are strictly adhered to, damage to the fabrics being bleached or sanitized can readily occur. This failure (commonly by the consumer) to adhere to the instructions for proper product use, is referred to by manufacturers as product "misuse". In the most common mode of misuse, the consumer deposits the composition directly upon the fabric in the absence of sufficient water to lower the quantity of available chlorine below that at which damage occurs. For example, such compositions may be deposited upon the fabric prior to completion of the washing machine "fill" cycle. This results in a very high aqueous concentration of available chlorine, which results in fabric or dye damage. Additionally, a normally alkaline laundry detergent may be added along with the bleach under conditions of misuse, severely compounding the problem.

The compositions of the present invention possess the unexpected property of precluding or minimizing damage of the foregoing type, even under the drastic conditions of misuse just specified. More specifically, under those conditions where the compositions are present at concentrations exceeding saturation with respect to the solvent, the system acts to inhibit the available chlorine, as to preclude fabric damage or fabric dye degradation.

In the present composition, the finished formulation should properly yield a pH, when measured above saturation in respect to the solvent, of less than about 5. A preferable pH is in the range of from about 3 to 5.

It must be appreciated that this value is actually quite low, since pH is a logarithmic function. It must also be noted that this range is not one normally encountered in laundry-type products, the range in the latter typically being from about 9.8 to 11.2. This latter typical range is between about 100,000 and 1,000,000 times more alkaline than that of the preferred embodiment of the present invention.

The invention is illustrated by the following Examples, which are considered to be illustrative only of the present invention, and should not be considered as limiting the invention which is otherwise defined in the claims:

EXAMPLE I

Samples of formulations representative of the invention, along with samples representative of formulations outside the invention, were prepared using standard mixing procedures well known to those skilled in the art. The pH of each sample was determined by employing a Perkin Elmer Metrion III pH meter along with a Corning glass electrode #476024 and a Corning Calomel ® reference electrode #476002. To prevent undesirable interactions between the chlorine-containing samples and the reference electrode, a salt bridge was employed. Salt bridges were prepared by treating cotton string in the following manner: 100% cotton string having a cross-sectional diameter of approximately 3 mm was cut into 6" pieces. These pieces were then boiled for 5 minutes to remove any impurities, such as sizing, from the string and, after cooling, were squeezed out by hand to remove most of the liquor. This procedure was repeated three times. The string sections were then placed in a suitable glass container and covered with a saturated solution of potassium chloride. Enough additional potassium chloride crystals were added to the jar to compensate for any plain water remaining in the strings, and to insure saturation. In actual pH determinations, the reference electrode was immersed in a beaker containing a saturated solution of potassium chloride. One end of a previously prepared salt bridge string was also immersed in this solution, and the other end of the bridge was immersed in the sample, along with the glass electrode. The salt bridge thus completed the necessary electrical connection while preventing unwanted interactions. All pH determinations were made at 25° C., employing a sample concentration of 50% by weight in water. This concentration was employed rather than the usual 1% solution since it more closely approximates the actual conditions encountered in a potential misuse situation. Since the indicated 50% by weight of the composition much exceeds the solubility of same in the water, this saturated admixture can be more properly referred to as "50% aqueous solution/-suspension".

The chemical make-up of each sample formulation is shown in Table 1, along with the pH determined for each sample. The dichlorinated hydantoins used in these formulations were 1,3-dichloro-5,5-dimethylhydantoin, and 1 bromo-3 chloro-5,5-dimethylhydantoin.

TABLE 1

| Formulation | Parts per Hundred | | | | | | | | | | |
|---|---|---|---|---|---|---|---|---|---|---|---|
| | A | B | C | D | E | F | G | H | I | J | K |
| 1,3-dichloro-5,5-dimethylhydantoin | 100 | | 50 | 50 | 50 | 50 | | 35 | | 50 | 35 |
| 1-bromo-3-chloro-5,5-dimethylhydantoin | | 100 | | | | | 50 | | 35 | | |
| Sodium phosphate, monobasic | | | | 40 | | 50 | 50 | | | | 35 |
| Boric acid | | | | | 50 | | | 35 | 35 | 30 | |
| Sodium borate-pentahydrate | | | 50 | | | | | | | | |
| Sodium polyacrylate | | | | 10 | | | | | | | |
| 5,5-dimethylhydantoin | | | | | | | | 30 | 30 | 20 | 30 |
| 50% Solution/Suspension pH | | | 9.0 | <5 | <5 | <5 | <5 | <5 | <5 | <5 | <5 |

EXAMPLE II

Each sample was also subjected to a damage test. In this test, denim cotton swatches measuring 4.5 cm×4.5 cm were each placed in the concave center of a watch glass having a diameter of 12.5 cm. A 3 gram portion of each sample along with a 3 gram portion of a normally alkaline laundry detergent was placed in the center of a swatch, and a 10 milliliter portion of tap water at 25°·C. with a hardness concentration of 50 ppm, as calcium carbonate, was carefully poured into each watch glass, care being taken not to pour the water directly on the swatch. The wetted samples were allowed to remain in intimate contact with the swatches for a period of five minutes, after which the swatches were removed from their respective watch glasses, rinsed for 30 seconds with cool tap water, and immersed in a 0.5% solution of sodium thiosulfate for a period of three minutes. The swatches were then air dried and any visual dye damage was noted. Degree of dye damage is shown in Table 2.

TABLE 2

| Formulation | A | B | C | D | E | F | G | H | I | J | K |
|---|---|---|---|---|---|---|---|---|---|---|---|
| Dye Damage Rating | 5 | 5 | 5 | 4 | 3 | 4 | 4 | 1 | 1 | 1 | 1 |

1 = no perceptible damage  3 = moderate damage  5 = severe damage

It is evident from the above that the formulations of the present invention are superior in their ability to prevent fabric and dye damage under misuse conditions.

EXAMPLE III

Pursuant to a further aspect of the invention, easily handleable homogeneous granules or pellets can be formed with the novel compositions of the invention without the necessity of using a separate binder, since the three major components, dihalohydantoin, dimethylhydantoin and acidifying agent, when mixed in the dry state along with sufficient water, form a setting mixture similar to that experienced with plaster of paris. Thus the compositions of this invention, when mixed with sufficient water, can be cast or extruded and allowed to harden into readily usable granules or pellets. Alternatively, the dry powdered mixtures can be sprayed with water in an agglomerator, such as a pan agglomerator, thus supplying the necessary reaction water to form discrete homogeneous granules.

By means of illustration, 1 part of 1,3-dichloro-5,5-dimethylhydantoin, 1 part of 5,5-dimethylhydantoin and 1 part of boric acid were mixed together in the dry state. Water was added to the dry mixture at the rate of 1 part water to 2 parts dry mixture and all components were thoroughly mixed to a thick paste. This paste was immediately transferred to a flat polyethylene mold having a series of parallel longitudinal grooved depressions 2 mm deep in its surface. The top of the mold was subsequently scraped off with a spatula allowing the wet mixture to reside only in the grooved depressions of the mold.

Upon setting and air drying the mold was flexed, thereby expelling the rods of hardened material. The rods were then broken into pieces averaging 2 mm long. The resulting pellets were found to be free flowing and easily handleable and sufficiently soluble such that one gram of pellets was able to be completely dispersed or dissolved in 200 ml of 50° F. water with gentle stirring.

EXAMPLE IV

An identical powder mixture was produced as described in Example III. In this instance, however, a coarse mist of water was sprayed on to the powder, and with simple agitation, discrete homogeneous particles of the composition were formed. Upon setting and air drying, these particles or pellets were also found to have good handling and solution characteristics.

The extrusion technique of Example III may be readily adopted to large scale pelletization, e.g. by subjecting the extrudate to periodic cutting or disruption, e.g. by a blade which periodically intercepts the advancing extrudate so that the latter is ejected as a series of discrete pellets—which are then dried.

EXAMPLE V

To demonstrate the bleaching effectiveness of the compounds of the invention, a bleach formulation was prepared according to the present teachings. To one part of 1,3-dichloro-5,5-dimethylhydantoin was added one part of 5,5-dimethylhydantoin, one part of boric acid and two parts water. The mixture was stirred and the resulting paste was spread onto a glass plate to a thickness of approximately 3 mm. Upon hardening, the resultant sheet of bleaching compound was broken into small pieces such that all material would pass through a #10 standard mesh screen. A typical laundry detergent (coded L) having the formula shown in Table 3 was prepared and to this was added the above prepared particulate bleach at a ratio of 0.15 parts bleach to 1 part laundry detergent. The combination of detergent L and bleach was coded M. A controlled wash test was then performed in a Tergo-tometer (U.S. Testing Co., Hoboken, N.J.) using the parameters shown in Table 4. Both coffee-stained and grape juice stained cotton swatches were employed in the test. Stain removal effectiveness was determined through swatch reflectance. Reflectance readings were made with a Hunter Reflectometer, and % stain removal was calculated using the formula:

$$\& \text{ Stain Removal} = \frac{Lw - Ls}{Lu - Ls}$$

Where
Lw = Washed Cloth Reflectance
Ls = Stained Cloth Reflectance
Lu = Unstained Cloth Reflectance Formulations tested along with results are shown in Table 5.

TABLE 3

Laundry Detergent L

| Ingredient | % By Weight |
| --- | --- |
| Sodium Carbonate | 21.0 |
| Sodium Silicate | 15.0 |
| Anionic Surfactant | 18.5 |
| Nonionic Surfactant | 1.5 |
| Optical Whitener | .15 |
| Carboxymethylcellulose | .50 |
| Sodium Sulfate | Q.S. |

TABLE 4

Test Parameters

| Wash Temperature | 80° F. |
| --- | --- |
| Water Hardness | 150 ppm as $CaCO_3$ |
| Speed | 110 rpm |
| Wash Time | 10 min. |
| Water Volume | 1 liter |
| Detergent Concentration | 0.20% |

TABLE 5

Products Tested and Results

| | % Stain Removal | |
| --- | --- | --- |
| | Coffee | Grape Juice |
| L | 30.5 | 56.8 |
| M | 78.4 | 86.2 |
| N* | 52.2 | 74.0 |

*Commercially available detergent/bleach combination: Tide with bleach (no phosphate), Proctor and Gamble Co.

It can be seen from the results set forth in Table 5 that formulation M, which is a typical laundry detergent in combination with a bleach prepared according to the present invention, removed significantly more stain than either the typical laundry detergent alone, or the nationally marketed detergent/bleach combination product.

While the present invention has been particularly set forth in terms of specific embodiments thereof, it is to be understood in view of the instant disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

What is claimed is:

1. An improved dry powder composition for use in aqueous solution in the bleaching and sanitizing of fabrics, which will cause minimal fabric or fabric dye damage upon direct contact of the concentrated composition with damp or wet fabric, said composition comprising:

a first component comprising a dry dialkyldihalohydantoin, which in aqueous solution provides a source of available bleaching and sanitizing chlorine; and a second component comprising an inhibiting system in an effective amount to inhibit the activity of available chlorine from the first component such that fabric or fabric dye degradation is beneath a predetermined level when the concentration of the first component of the composition is above saturation with respect to the aqueous solvent; said inhibiting system comprising 5,5-dimethylhydantoin, and one or more dry acidifying agents which function to buffer a 50% aqueous solution/suspension of said composition to a pH of 5.0 or below, the weight ratio of said acidifying agent being in the range of from 0.5 to 10 parts, per 10 parts of total combined dialkyldihalohydantoin and dimethylhydantoin.

2. A composition in accordance with claim 1, wherein the weight ratio between said dialkyldihalohydantoin and said dimethylhydantoin is in the range of from 1:10 to 10:1.

3. A composition in accordance with claim 2, wherein the weight ratio between said dialkyldihalohydantoin and said dimethylhydantoin is in the range of from 1:2 to 2:1.

4. A composition in accordance with claim 3, wherein the weight ratio of said acidifying agent is in the range of from 1 to 5 parts per 10 parts of total combined dialkyldihalohydantoin and dimethylhydantoin.

5. A composition in accordance with claim 1, wherein the said dry acidifying agents are selected from one or more members of the group consisting of boric acid, citric acid, oxalic acid, and sodium or potassium phosphate monobasic.

6. A composition in accordance with claim 1, including additional builders.

7. A pelletized powder composition for use in aqueous solution in the bleaching and sanitizing of fabrics, which will cause minimal fabric or fabric dye damage upon direct contact of the concentrated composition with damp or wet fabric, said composition comprising:

an admixture of a dry dialkyldihalohydantoin which in aqueous solution provides a source of available bleaching and sanitizing chlorine; with an inhibiting system in an effective amount to inhibit the activity of available chlorine from the first component such that fabric or fabric dye degradation is beneath a predetermined level when the concentration is above saturation with respect to the aqueous solvent; said inhibiting system comprising 5,5-dimethylhydantoin, and one or more acidifying agents which function to buffer a 50% aqueous solution/suspension of said composition to a pH of 5.0 or below, the weight ratio of the acidifying agent being in the range of from 0.5 to 10 parts, per 10 parts of total combined dialkyldihalohydantoin and dimethylhydantoin.

8. A composition in accordance with claim 7, wherein the weight ratio between said dialkyldihalohydantoin and said dimethylhydantoin is in the range of from 1:10 to 10:1.

9. A composition in accordance with claim 8, wherein the weight ratio between said dialkyldihalohydantoin and said dimethylhydantoin is in the range of from 1:2 to 2:1.

10. A composition in accordance with claim 9, wherein the weight ratio of acidifying agent can vary from 0.5 to 10 parts, per 10 parts of total combined dialkyldihalohydantoin and dimethylhydantoin.

11. A composition in accordance with claim 7, wherein said acidifying agents are selected from one or more members of the group consisting of boric acid, citric acid, oxalic acid and sodium or potassium phosphate monobasic.

12. A composition in accordance with claim 7 wherein said pellets are free of organic binders.

13. A method of laundering a fabric comprising washing said fabric in a solution or suspension which contains a composition which causes minimal fabric or fabric dye damage upon direct contact between the composition and damp or wet fabric, said composition being comprised of
(a) a first component which is further comprised of a dry dialkyldihalohydantoin, which in solution provides a source of available bleaching and sanitizing chlorine, and
(b) a second component comprised of an inhibiting system which is present in the composition in an amount effective for inhibits the activity of available chlorine from the first component, such that fabric or fabric dye degradation is beneath a predetermined level when the concentration of the first component of the composition is above saturation with respect to the aqueous solvent, said inhibiting system comprising 5,5-dimethylhydantoin, and one or more acidifying agents which function to buffer a 50% aqueous solution/suspension of said composition to a pH of 5.0 or below, the weight ratio of said acidifying agent being in the range of from 0.5 to 10 parts to 10 parts of total combined dialkyldihalohydantoin and dimethylhydantoin.

* * * * *